United States Patent [19]

Doyle

[11] Patent Number: 5,418,615
[45] Date of Patent: May 23, 1995

[54] PROBE FOR LIQUID SAMPLE ANALYSIS BY LIGHT TRANSMISSION

[75] Inventor: Walter M. Doyle, Laguna Beach, Calif.

[73] Assignee: Axiom Analytical, Inc., Irvine, Calif.

[21] Appl. No.: 201,792

[22] Filed: Feb. 25, 1994

[51] Int. Cl.⁶ .................... G01N 21/01; G01N 21/59
[52] U.S. Cl. ...................................... 356/436; 356/442
[58] Field of Search ............... 356/436, 441, 442, 436, 356/440; 250/573, 576

[56] References Cited

U.S. PATENT DOCUMENTS

| | | | |
|---|---|---|---|
| 3,164,663 | 1/1965 | Gale | 356/436 |
| 4,534,651 | 8/1985 | Minikane | 250/576 |
| 4,893,935 | 1/1990 | Mandel et al. | 356/442 |
| 4,989,942 | 2/1991 | Koenigsberg et al. | 356/436 |

FOREIGN PATENT DOCUMENTS

| | | | |
|---|---|---|---|
| 1959612 | 6/1971 | Germany | 356/432 |
| 25239 | 2/1987 | Japan | 356/436 |

*Primary Examiner*—Richard A. Rosenberger
*Attorney, Agent, or Firm*—Thomas J. Plante

[57] ABSTRACT

A probe for liquid sample analysis is disclosed which causes radiation to pass through the sample at a gap formed in the probe housing. A single radiation transmission is used to avoid problems of radiation back scatter and sample reliability. Windows are provided on opposite sand and and and and and and and ides of the gap to accommodate the shape of the beam in the gap, which may either be collimated, or focused in the gap. A retroreflector may be used to reverse the radiation direction in the probe. The light to and from the probe is preferably transmitted by optical fiber cables. Within the probe, light guides other than optical fibers may be used.

10 Claims, 7 Drawing Sheets

PROBE FOR LIQUID SAMPLE ANALYSIS BY LIGHT TRANSMISSION

BACKGROUND OF THE INVENTION

This invention relates to probes which can be inserted into liquid samples, for the purpose of using radiation transmitted through a sample to obtain spectroscopic information. The light wavelengths commonly used are in the range of 0.8 microns to 4.5 microns. The preferred method of sending light between the analytical instrumentation and the probe is fiber optic transmission.

Probes heretofore available for this purpose generally have had two major problems. One problem is excess stray light (e.g., 10% stray light) due to backscatter from air bubbles and particulate matter in the liquid sample. Another problem is sample retention due to a large gap cross-section combined with the short transmission pathlength used for many samples.

SUMMARY OF THE INVENTION

The present invention uses a single pass of light through the sample, instead of two passes. This eliminates backscatter as a source of stray light. Also the problem of liquid retention is reduced because (a) the total window area at the gap is reduced, and (b) the distance across the gap is twice as great for a given optical pathlength through the sample.

DETAILED DESCRIPTION OF SPECIFIC EMBODIMENTS

Figure 1:
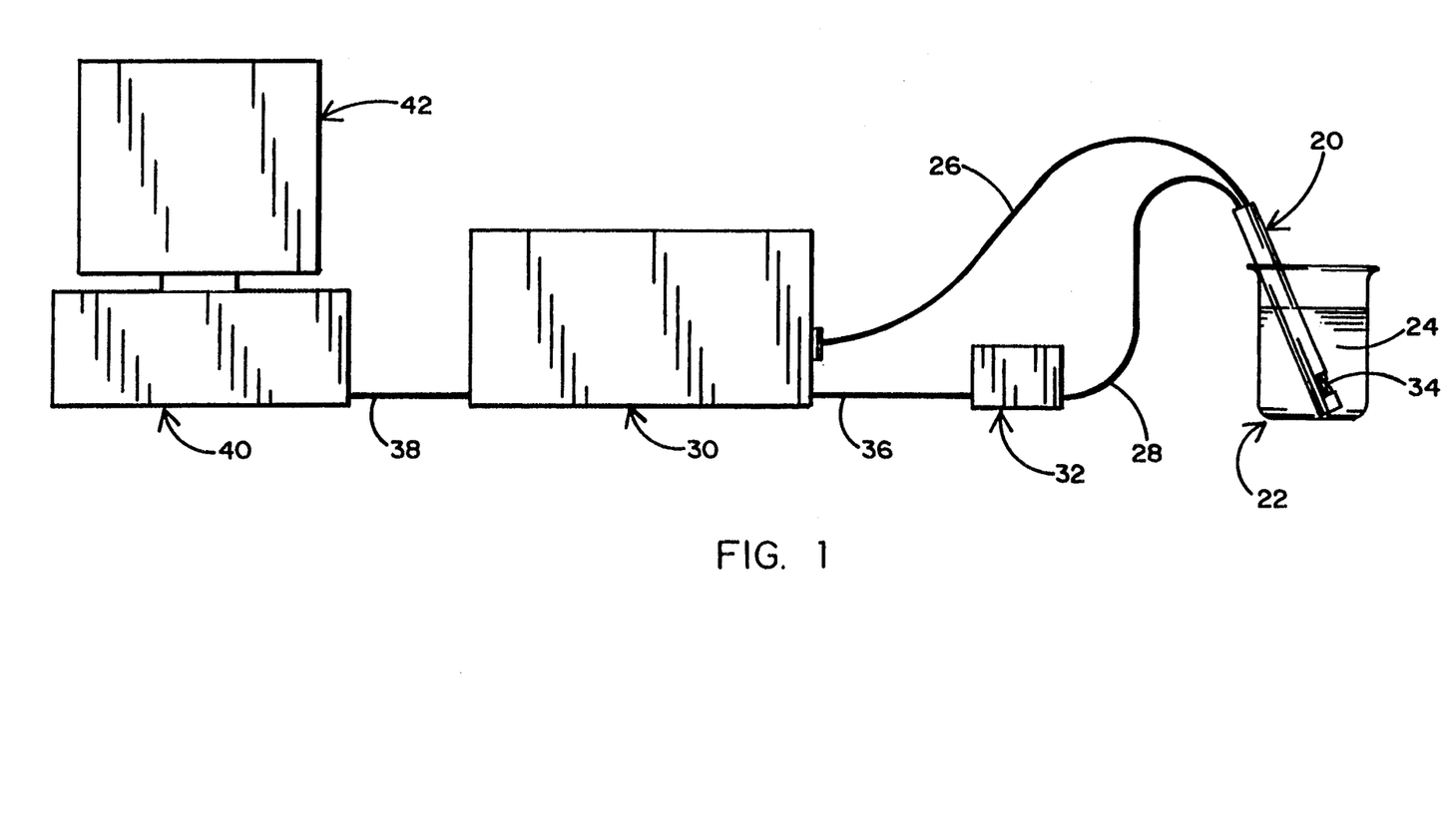
FIG. 1 diagrams a system in which the probe of the present invention might be used.
Figure 2:
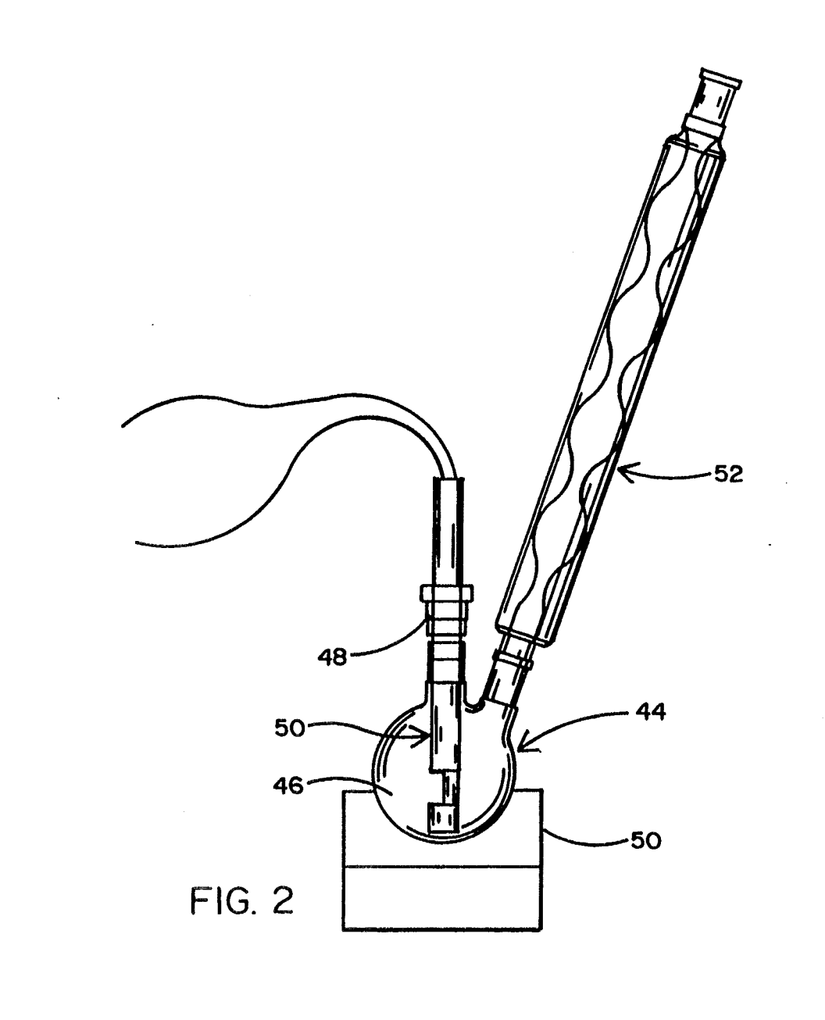
FIGS. 2 and 3 show other possible uses of the probe.
Figure 3:
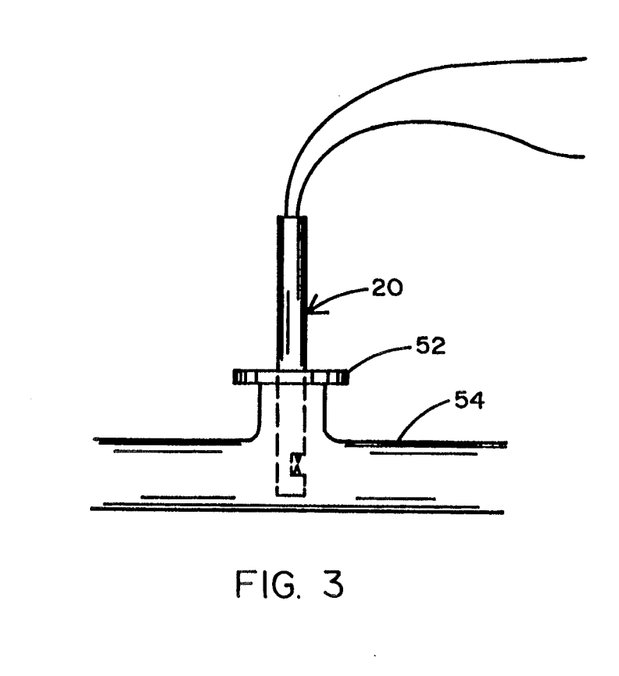

FIGS. 1-3 illustrate some of the uses of a transmission probe. In FIG. 1, a transmission probe 20 is shown resting in a beaker 22, which contains a fluid sample 24. From the upper end of the probe 20, two fiber optic cables 26 and 28 extend. Fiber optic cable 26 extends to a spectrometer 30; and fiber optic cable 28 extends to a detector assembly 32.

Spectrometer 30 may be the interferometer part of an FTIR spectrometer, or a dispersive spectrometer, or a filter spectrometer. Its function is to divide light up according to its wavelengths, and to scan the various wavelengths. The cable 26 transmits the light signals from the spectrometer 30 to the probe. In the probe, the light is caused to be transmitted through the liquid which is present in a gap 34 formed in the probe housing.

From probe 20, sample-altered light signals are transmitted by cable 28 to the detector assembly 32, e.g., an infrared detector and a preamplifier. From the detector assembly 32, an electrical line 36 carries electronic signals to the spectrometer 30, where the electronic relationship between outgoing and incoming signals can be monitored. The electronic output signal from the spectrometer box 30 is transmitted by line 38 to a computer 40, which has a display 42.

FIG. 2 shows a round-bottomed reaction vessel 44, useable as a laboratory flask. The probe 20 extends into a chamber 46 through a fitting 48. A heating mantle 50 surrounds the bottom of the flask. A chemical condenser 52 may be connected to the flask. The probe 20 may be used to monitor a chemical reaction as it occurs. If necessary, a stirring mechanism (not shown) may be included, in order to insure that the sample illuminated by the probe accurately represents the liquid in the flask.

FIG. 3 shows probe 20 extending through a flange 52 into a pipe 54. The sample liquid flows in the pipe.

Figure 4:
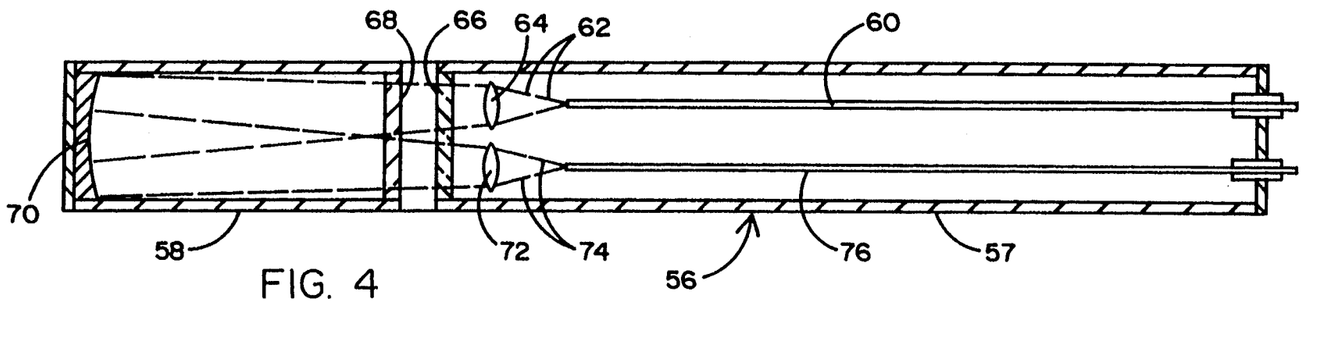
FIGS. 4-6 show schematically three different prior art probes, each having a double pass of radiation through the sample.
Figure 5:
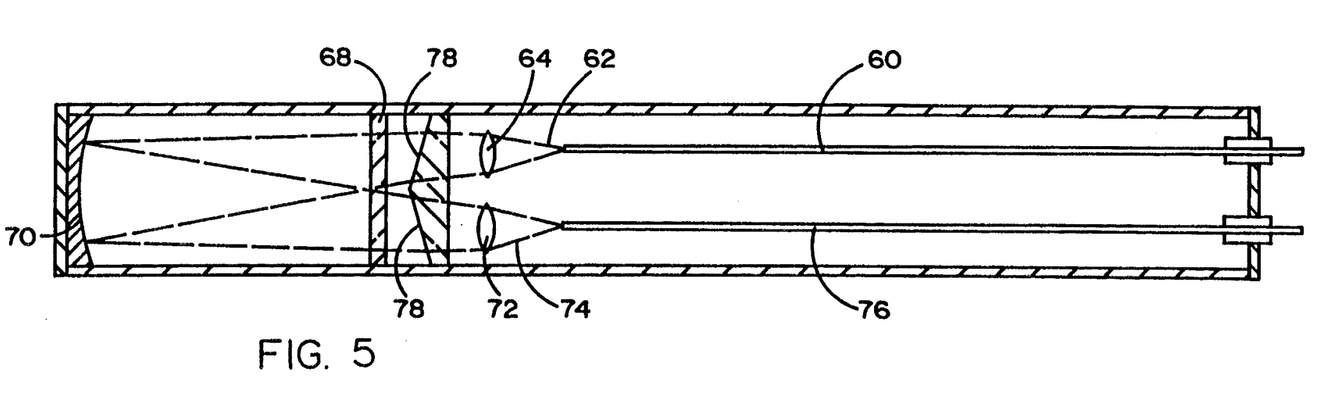
Figure 6:
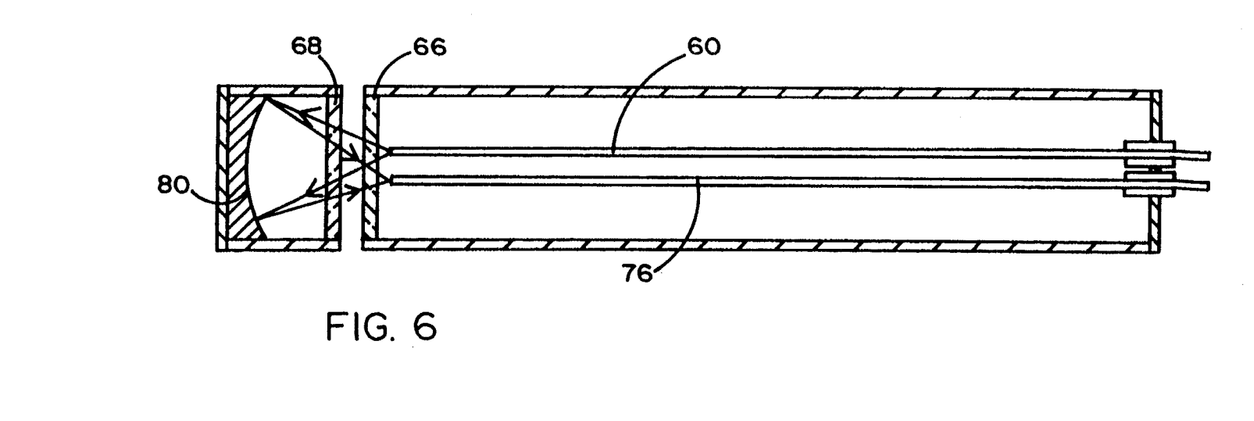

FIGS. 4-6 show three double pass probes, which illustrate the problems encountered with existing transmission probe devices. In the configuration shown in FIG. 4, the probe 56 has two enclosed sections 57 and 58 which are connected by a mechanical structure (not shown). Visible or infrared radiation is brought into the probe by a fiber optic cable 60. This typically is a single fiber having a fairly large diameter (200 to 600 $\mu$m). Light emerging from the end of this fiber will typically diverge as shown by path 62, with an included angle of 30 degrees (numerical aperture=0.5). This is collected by a lens 64 and directed through a pair of windows 66 and 68, the separation between which determines the transmission pathlength through the sample. In this region, the light will continue to diverge but with a reduced included angle—as determined by the diameter of the fiber and the distance between it and the collecting lens 64.

The second window 68 defines one end of the second enclosed section 58 of the probe. The two sections of the probe are so connected as to allow the sample to flow through the gap between the windows 66 and 68. Within the second section 58 of the probe, the light continues to diverge until it strikes a mirror 70. In the design illustrated, this is a spherical mirror with its center of curvature located midway between the transmitting lens 64 and a symmetrically positioned receiving lens 72. The mirror 70 thus images the transmitting lens on the receiving lens. Some designs employ a flat mirror, which obviously results in reduced optical coupling efficiency. After the radiation passes through lens 72, it converges, as shown by path 74, to enter a fiber optic cable 76, which transmits it out of the probe.

The dashed lines in FIG. 4 represent the fields of view of the two lenses 64 and 72. As shown, these fields overlap only partially, thus limiting coupling efficiency. At least one design minimizes this problem by using a wedge shaped window 78, as shown in FIG. 5. The wedge-shaped window 78 causes a closer convergence at mirror 70 of the entering and exiting radiation paths, as shown by the dashed lines in FIG. 5. However, the wedge-shaped sample volume between windows causes non-linearity in the light transmission pattern.

FIG. 6 shows a simpler design, in which a single curved reflector 80 is used to image the end of one fiber (60) on the end of the other fiber (76). In principle, this provides relatively high coupling efficiency since, without the use of collimating lenses, the fields of view of both fibers will be highly overlapping at the reflector. As with the other prior art designs, a pair of windows 66 and 68 are used to define the sample gap.

The design shown in FIG. 6 has two major faults. First, the use of widely diverging radiation paths results in a wide range of angles of propagation in the sample gap, and hence a wide range of pathlengths. This will lead to significant data nonlinearity.

The second fault results from the fact that the fields of view of the two fibers overlap within the sample gap, and at the surfaces of the windows. Backscatter from these surfaces and from bubbles or particles in the sample will be a significant source of stray light.

In general, the double pass transmission probe designs are plagued by the twin problems of stray light and sample retention. The stray light results from radiation being reflected by the window surfaces and scattered by minute air bubbles and particulate matter within the sample fluid. Some of the scattered light reaches the receiving lens after following a path which is substantially different from the intended path. Depending on the pathlength being used, this behavior can lead to a significantly nonlinear response (i.e., absorbance as a function of sample concentration). The effect is most pronounced for relatively long paths.

The sample retention problem results from the fact that the current double pass designs employ fairly large windows in order to transmit both the outgoing and returning beams. It is exacerbated by the fact that the effective sample thickness is twice the separation between the two windows. For a strongly absorbing sample, achieving the optimum sample thickness to avoid excessive absorbance of light may require a window separation which is small compared to the window diameter. If the sample is viscous as well as strongly absorbing, it may not be possible to insure a continuous flow of sample through the gap. The sample retained in the gap will obviously not represent the current conditions in the bulk of the liquid.

Figures 7, 8:
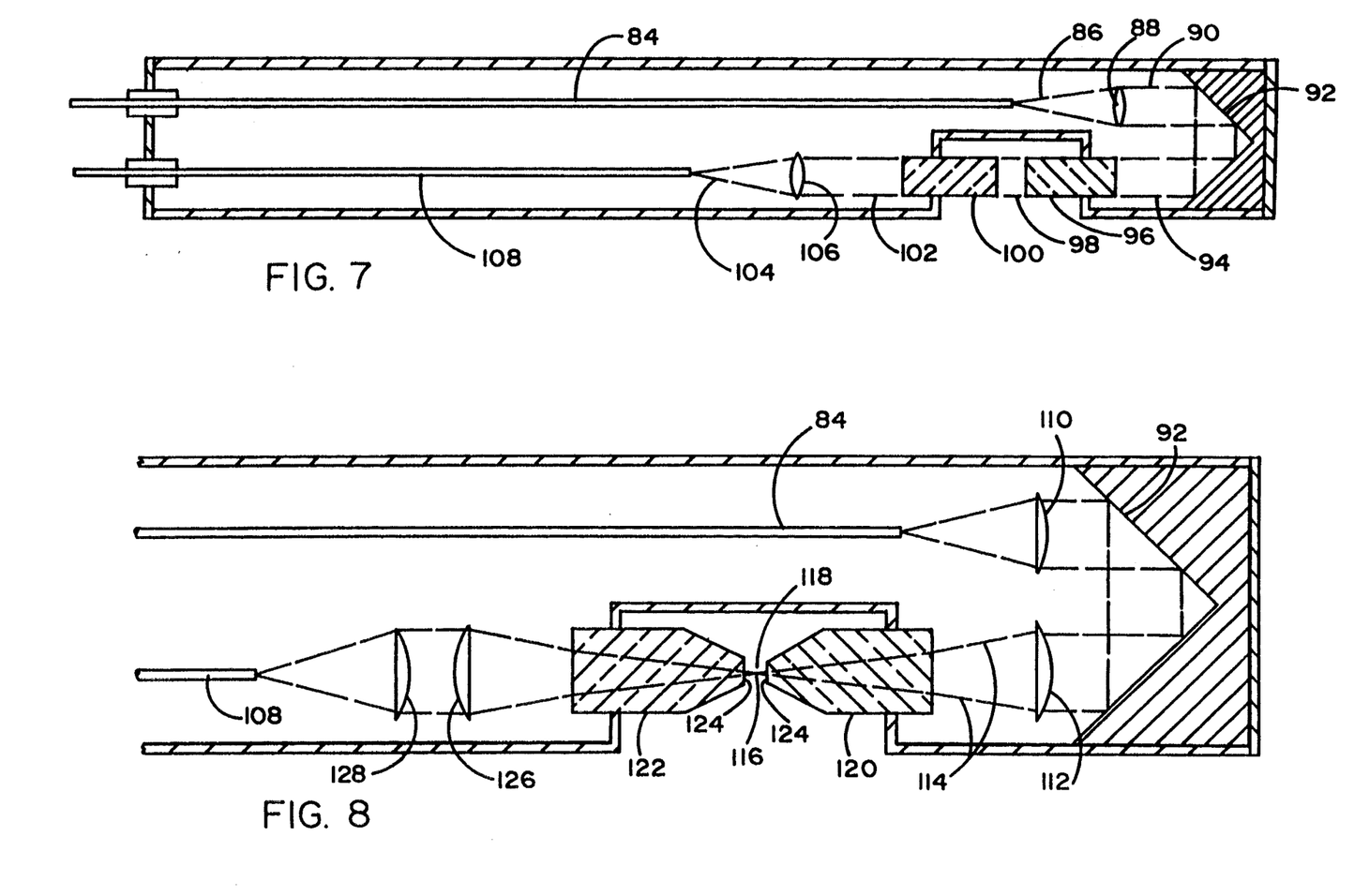
FIGS. 7-12 show six different embodiments of the present invention.

The present invention differs from previous transmission probes by using a single pass through the sample, rather than two passes. One embodiment is shown in FIG. 7. A major difference between this design and the double pass design shown in FIGS. 4–6 is the fact that either the incoming or the outgoing optical beam is enclosed within the probe structure, so that it is not exposed to the sample. Also, the collimated beam travelling near the end of the probe is reversed in direction by a retroreflector. This maximizes the transfer of optical power from the incoming path to the outgoing path. The retroreflector can be a cube corner, a 90° cone, or a 90° rooftop mirror.

In FIG. 7, either of the two fiber optic cables may transmit the incoming, pre-sample light. The other will transmit the exiting, post-sample light. Assume that the incoming light is transmitted by cable 84. Light exiting from cable 84 has a diverging beam 86, which is collected by a lens 88, and converted into a collimated beam 90. The direction of collimated beam 90 is reversed by a retroreflector 92, and the beam follows path 94 to a window 96. After passing through window 96, the light continues as a collimated beam through gap 98 filled with sample liquid, and enters a window 100. The sample-altered beam is converted from a collimated beam 102 to a converging beam 104 by a lens 106. The light then enters a fiber optic cable 108 to exit the transmission probe.

In the embodiment shown in FIG. 7, the optical beam is nominally collimated in the sample gap 98. This gap is formed by the pair of optical windows 96 and 100, which are designed to allow adjustable spacing of the surfaces forming the gap. If these windows are made sufficiently thick, a wide range of spacings will be possible.

The probe design shown in FIG. 7 has three advantages compared to the double pass designs. First, with a single pass, backscatter does not constitute a source of stray light. Second, the area of the gap is equal to the window area required only to transmit a single beam rather than having to encompass both of the spaced beams. Third, for a given optical pathlength through the sample, the physical gap will be twice as great as with the two path design. These latter two advantages substantially reduce the problem of sample retention, thus ensuring the presence of a representative sample in the light transmission gap.

A second embodiment of the present invention is shown in FIG. 8. In this version, the radiation passes through a focus in the center of the sample gap. This allows the windows to be tapered down to a much smaller cross-section at the gap, further reducing the possibility of sample retention. With the design shown in FIG. 8, the gap spacing can be varied by simply moving one or both windows, as in the case of FIG. 7.

In FIG. 8, entering light from fiber optic cable 84 is collected and collimated by a lens 110, redirected by a retroreflector 92, and then focused by a lens 112. The shape of the lens used depends on the lens material, focal distance, etc. There is no significance in the fact that lenses 88 and 106 in FIG. 7 are shown as bi-convex, whereas lenses 110 and 112 in FIG. 8 are shown as plano-convex.

The radiation path 114 leaving lens 112 converges to focus at 116 in the gap 118 between two windows 120 and 122. Because of the focusing beam, windows 120 and 122 may be tapered down to have surface areas 124 which are much smaller than the surface areas of windows 96 and 100 in FIG. 7. The reduced area enhances sample flow in gap 118. Exiting radiation from window 122 passes through lenses 126 and 128 to enter the fiber optic cable 108. As in the structure of FIG. 7, the size of gap 118 in FIG. 8 may be adjusted by moving one of the windows 120 or 122.

Figure 9:
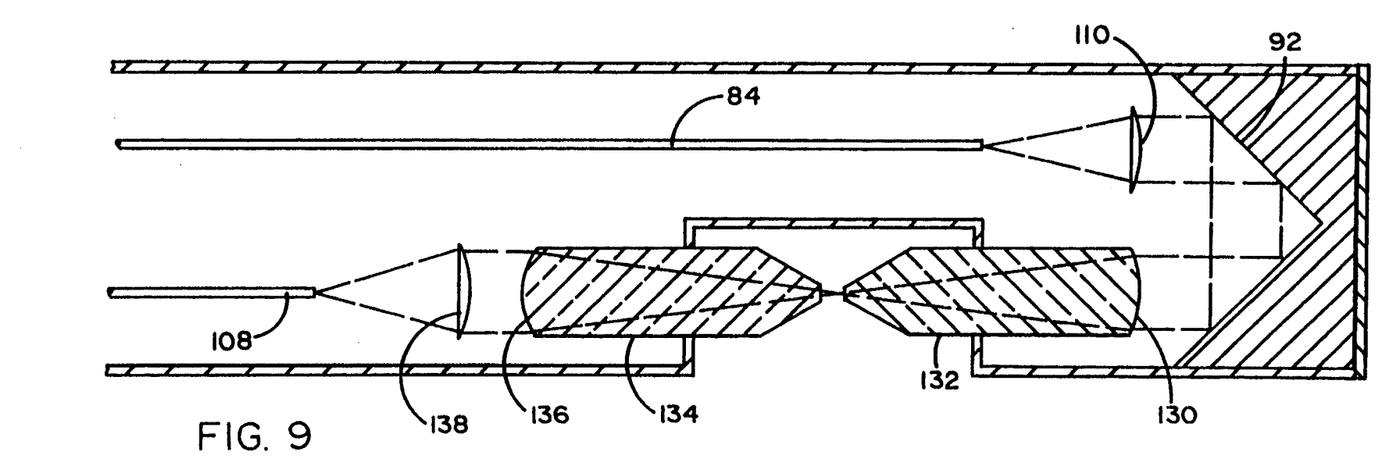

FIG. 9 shows an embodiment in which the focusing lenses are integral to the tapered windows. This design simplifies construction and minimizes reflection losses by reducing the number of optical elements. It also makes it possible to convert between the collimated geometry of FIG. 7 (appropriate for large gaps) and the focused geometry of FIG. 9, by merely changing the windows. On the other hand, it does limit the range over which the transmission path length can be varied by displacing a window, since this will also defocus the optical beam, hence reducing transmission.

In FIG. 9, entering light from fiber optic cable 84 is collected and collimated by a lens 110, and redirected by a retroreflector 92. Focusing of the collimated beam is accomplished by the curved surface 130 formed as the end surface of a window 132. Except for the curvature of surface 130, window 132 is similar to window 120 of FIG. 8. The opposite window 134 has a curved surface 136, through which the exiting light passes. The surface 136 collimates the light, which is then focused by a lens 138 on fiber optic cable 108.

Figure 10:
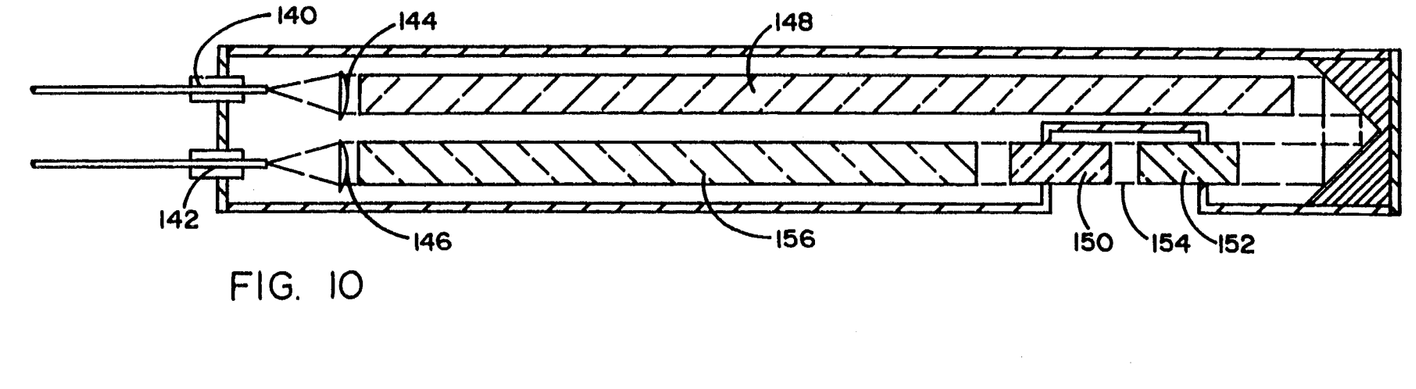

FIGS. 7, 8, and 9 all show the optical fiber portion of the system extending well into the probe. In some cases—such as those involving very high temperatures or nuclear radiation—this may not be desirable. FIG. 10 shows a design which avoids this problem. Here the optical fibers are terminated in the upper (near) region of the probe, and their diverging fields of view are converted to collimated beams by appropriately placed lenses. The collimated beams are then transmitted to the lower (far) region of the probe by means of macroscopic light guides. These can be either solid glass (or other dielectric material), or metallic optical pipes having highly reflective interior surfaces. This arrangement can be used with all three of the embodiments shown in FIGS. 7, 8, and 9.

In FIG. 10, fiber optic cables 140 and 142 terminate just inside the probe. Lenses 144 and 146 convert the radiation between expanding or diverging paths and collimated paths. The cables 140 and 142 are interchangeable as entering or exiting light paths. Between lens 144 and retroreflector 92, a light guide 148 transmits collimated radiation. Windows 150 and 152 are separated by sample gap 154. Between lens 146 and window 150, a light guide 156 transmits collimated radiation.

Figure 11:
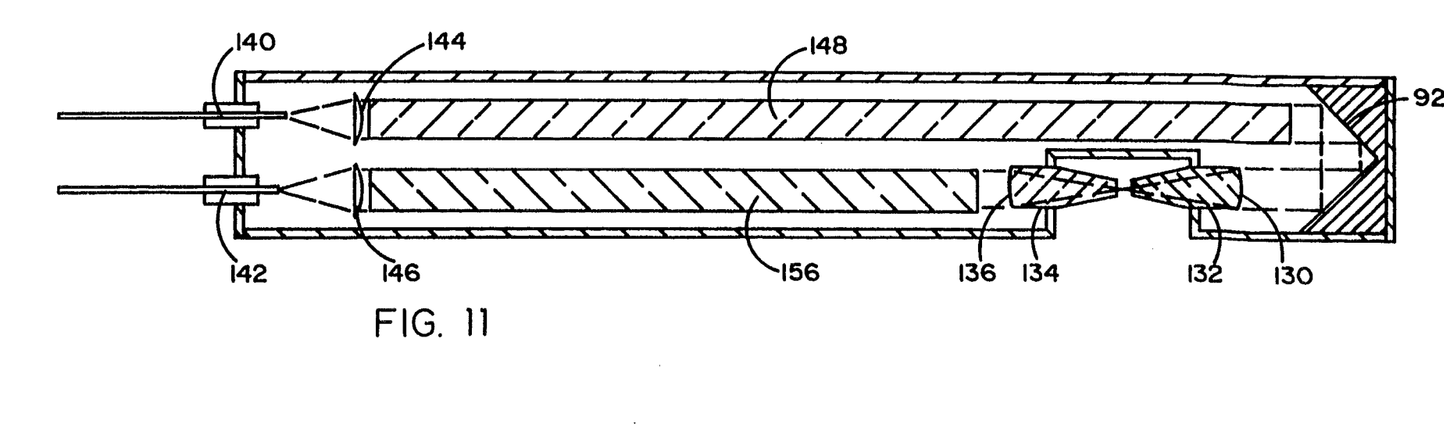

FIG. 11 illustrates the presently preferred embodiment. It combines the cable and light guide arrangement of FIG. 10 with the window structure of FIG. 9. Fiber optic cables 140 and 142 terminate just inside the probe. Lenses 144 and 146, and light guides 148 and 156, are as shown in FIG. 10. Windows 132 and 134, having curved lens-like end surfaces 130 and 136, are as shown in FIG. 9.

Figure 12:
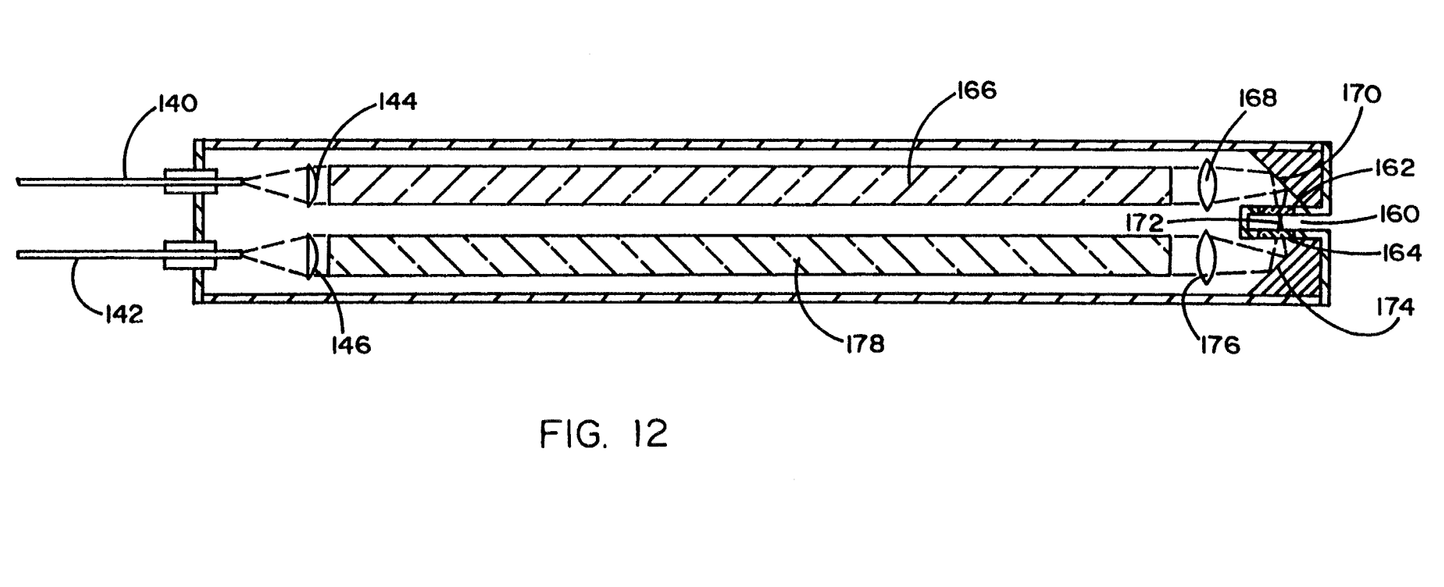

Another embodiment is shown in FIG. 12. In this version the gap for liquid illumination is located at the lower (remote) end of the probe, rather than in one side of the probe. This has the benefit of reaching the sample at the deepest end of the probe. A gap 160 is formed at the lower end of the probe (right end as seen in FIG. 12). Windows 162 and 164 are on opposite sides of the gap. Assuming that fiber optic cable 140 is the light entering cable, and that fiber optic cable 142 is the light exiting cable, light transmitted by cable 140 will be collimated by lens 144, and then transmitted as a collimated beam by a light guide 166. A lens 168 will create a converging light path which is reflected by a flat mirror 170 in such a way as to focus at 172 in the gap 160. After focusing at 172, the light path will diverge, and be reflected by flat mirror 174 to lens 176. Lens 176 will collimate the light path, causing it to be transmitted as a collimated beam by a light guide 178. At the left end of the probe, lens 146 will change the collimated beam to a focused beam which enters fiber optic cable 142.

From the foregoing description, it will be apparent that the apparatus and process disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A probe adapted to extend into a liquid sample to cause radiation transmission through the sample material, comprising:
   a housing enclosing the probe elements;
   first and second fiber optic radiation transmission lines extending to the housing to transmit incoming and outgoing radiation toward and away from the sample, said fiber optic lines being terminated where they enter the housing;
   a single sample gap provided by the housing to receive sample liquid through which the radiation passes only once;
   first and second windows supported in the housing and located on opposite sides of the sample gap;
   a first lens structure which collects and collimates entering radiation from the first fiber optic line;
   a first macroscopic linear light guide which conveys the collimated entering radiation toward the first window;
   a second macroscopic linear light guide which conveys collimated exiting radiation away from the second window; and
   a second lens structure which receives and focuses the exiting radiation into the second fiber optic line.

2. The probe of claim 1 in which the fiber optic radiation transmission lines enter the same end of the housing, and the probe includes:
   means located near one end of the housing to reverse the direction of the radiation in the probe.

3. The probe of claim 2 wherein the direction of the radiation is reversed by a retroreflector.

4. The probe of claim 1 in which the radiation beam in the gap between the windows is collimated.

5. The probe of claim 4 in which:
   the windows are essentially cylindrical in cross-section.

6. The probe of claim 1 which includes:
   optical elements in the housing which cause the radiation beam to focus at a point in the gap between the windows.

7. The probe of claim 6 in which:
   the windows are tapered down so that their smallest cross-sectional area is at the gap.

8. The probe of claim 7 in which:
   the surface of each window furthest from the gap is convexly curved to act as a focusing lens.

9. The probe of claim 6 in which:
   the surface of each window furthest from the gap is convexly curved to act as a focusing lens.

10. The probe of claim 1 in which the first and second macroscopic light guides are solid rods formed of light-conducting material.

* * * * *